United States Patent [19]

Rosendal

[11] Plant 5,203

[45] Mar. 13, 1984

[54] EXACUM AFFINE POT PLANT

[75] Inventor: Erik Rosendal, Assens, Denmark

[73] Assignee: Nurserymen's Exchange, San Francisco, Calif.

[21] Appl. No.: 467,076

[22] Filed: Feb. 16, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—John T. Roberts; Richard H. Stern

[57] ABSTRACT

A new and distinct variety of Exacum plant characterized by double flowers, floriferousness, blooming habits and the sterility of the flower. Plants can be propagated by asexual processes true to type and the rooting ability is excellent. The size of the single flower surpasses the known single cultivars.

2 Drawing Figures

BACKGROUND OF THE NEW PLANT

The present new variety was discovered by me in a commercial greenhouse in Denmark as a spontaneous mutant within a large number of Exacum Affine Balf. cultivar "Midget" grown as pot plants.

Asexual propagation of new cultivar by cutting in my greenhouse through several generations proved that the new cultivar is true to type and constant in its characteristics. Color readings were taken Dec. 30, 1982 based on The Royal Horticultural Society's Colour Chart.

DESCRIPTION OF THE DRAWINGS

The new plant is illustrated in the accompanying drawings in which FIG. 1 is a full-color photograph of a potted plant in full bloom and FIG. 2 is a full-color photograph of the blossoms of the plant.

BRIEF SUMMARY

Exacum 'Rococo' is a characteristic new mutant of a known seed propagated cultivar 'Midget' and distinguished from its origin:

1. The flowers are double.
2. Growth rate is equal to single-flowered seed-propagated cultivars.
3. Growth habit as potted plants is compact with excellent branching ability.
4. Flowers are larger than the single-flowered cultivars.
5. Stigma and stamens are absent as they have become petalloid.
6. The flowers are sterile and produce no seed.
7. Reproduce easily with cuttings.
8. The keepability of the flower is better than for single-flowered cultivars.

The accompanying color photograph illustrates the overall appearance of the cultivar 'Rococo'. The color is slightly dependent on prevailing light condition. The following is based on observation on an overcast day and made Dec. 30, 1982.

DESCRIPTION OF THE DRAWINGS

PLANT

Origin: Mutation in a well-defined seed grown cultivar 'Midget.'

Form: Upright with heavy branching ability right from base to terminal shoots.
Height: To flowering, 18–25 cms.
Plant diameter: Similar to height.
Growth rate: Fast under good light conditions.
Type of cutting: Terminal shoots or stem segments.
Rooting time: 12–14 days.
Rooting habit: Fast and dense.

FOLIAGE

Arrangements: Opposite leaves at the bottom of all nodes.
Shape of leaves: Cordate.
Tip: Rounded.
Base: Round to cordate.
Margin: Entire.
Venation: Three-veined from petiole.
Size: Leaf-blade and petiole 40–48 mm; Length of blade 28–32 mm; Width at widest point 32–35 mm.
Surface: Smooth, slight crinkled.
Texture: Glabrous.
Variegation: None.
Color:
*Petiole.*—144 C.
*Veins.*—145 B.
*Leaf surface.*—137.
*Leaf underside.*—143 B.

STEM

Color: 144 B — by internodes purplish tinted.
Length of internodes: 30–35 mm.
Structure: Strong, rounded quadrangular.
Breaking action: Sympodial; One flower terminal at each node and two side shoots.

FLOWER

Form: Round.
Born: Terminal, single at the end of each ode.
Bud: Round 20–23 mm in diameter. Color 145 B.
Calyx: 5 winged. Color 143 A.
Petals: The number variates from 20–25. Outer petals arranged as a collar around a 6–8 mm tight ball of incurved petals changing in color from greenish to bluish while a fully open flower will normally consist of 14–16 spreading petals.
Petal color: 92 A to 90 C. Reverse side 92 C.
Lasting quality: Average keepability one week depending on temperature.

Behavior: The large number of flowers appear as an eye sight at the surface of the compact green foliage; Wilted flowers bend down and do not spoil the general appearance as much as by single-flowered cultivars.

Pedicels: 35–40 mm purplish green.

Having thus disclosed my invention, I claim:

1. A new and distinct variety of Exacum plant as shown and described, characterized by its double flowers, its floriferousness, its blooming habits and the sterility of the flower. Plants can be propagated by asexual processes true to type and the rooting ability is excellent. The size of the single flower surpasses the known single cultivars.

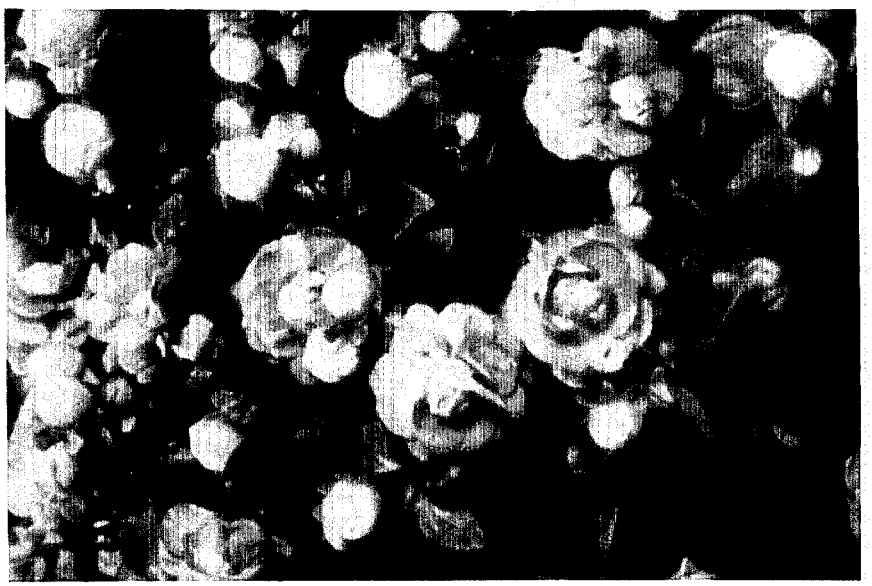
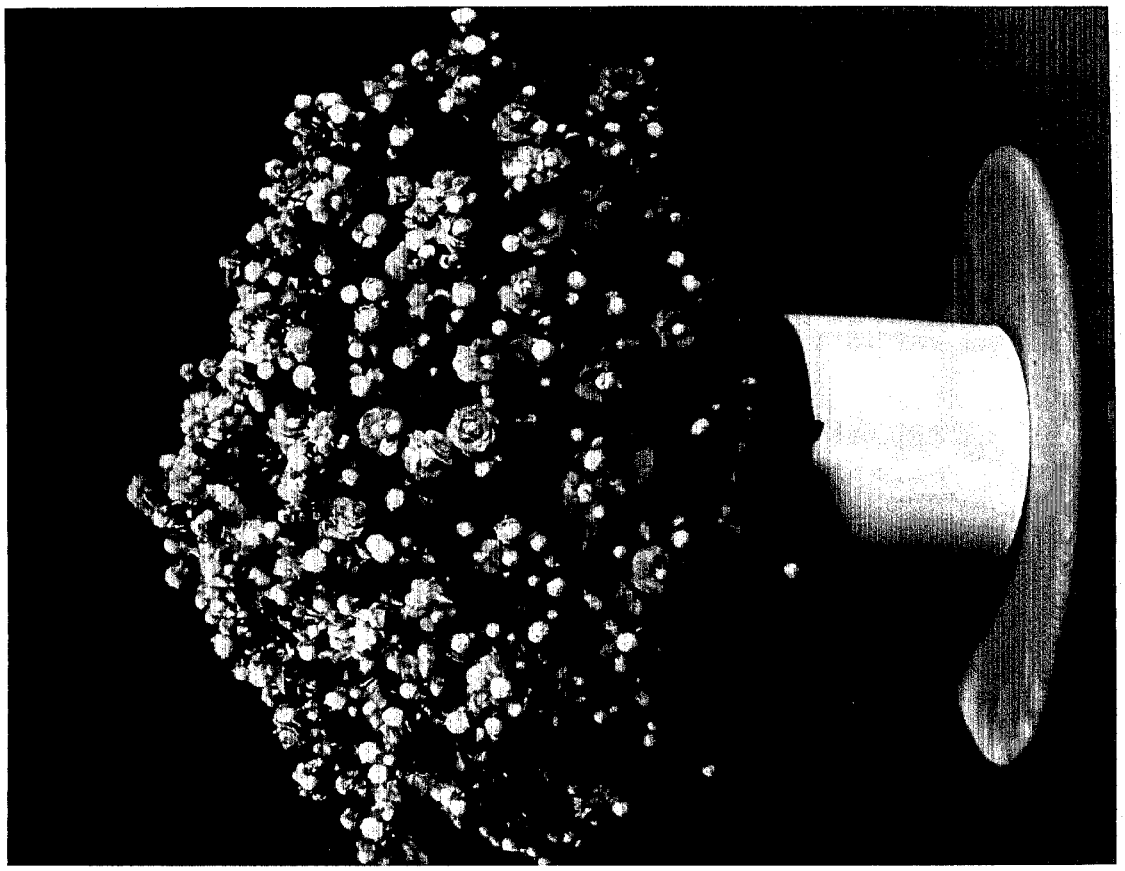

* * * * *